United States Patent [19]

Kopchick et al.

[11] Patent Number: 4,686,098
[45] Date of Patent: Aug. 11, 1987

[54] ENCAPSULATED MOUSE CELLS TRANSFORMED WITH AVIAN RETROVIRUS-BOVINE GROWTH HORMONE DNA, AND A METHOD OF ADMINISTERING BGH IN VIVO

[75] Inventors: John J. Kopchick, Verona; Frederick C. Leung, Scotch Plains; Thomas J. Livelli, Lyndhurst; Richard H. Malavarca, South Orange, all of N.J.

[73] Assignee: Merck & Co., Inc., Rahway, N.J.

[21] Appl. No.: 609,924

[22] Filed: May 14, 1984

[51] Int. Cl.$^4$ ............. A61K 9/44; A01N 25/10; C12N 11/02; C12N 11/04
[52] U.S. Cl. .................. 424/424; 424/438; 514/12; 435/177; 435/182; 604/891
[58] Field of Search ............. 435/177, 182; 424/33, 424/15; 514/12; 604/891

[56] References Cited

U.S. PATENT DOCUMENTS 4,391,909  7/1983  Lim ..................... 435/182

OTHER PUBLICATIONS

Hymer et al., Neuroendocrinology, 32:339–349 (1981).
Woychik et al., Nucleic Acids Research, 10:7197–7210 (1982).

*Primary Examiner*—Ronald W. Griffin
*Attorney, Agent, or Firm*—Donald J. Perrella; Hesna J. Pfeiffer

[57] ABSTRACT

Recombinant DNA constructs having an avian retroviral long terminal repeat (LTR) ligated to the bovine growth hormone gene, were co-transformed into a mammalian cell (mouse) culture in order to obtain a stable cell culture secreting large amounts of bovine growth hormone. The transformed mouse cells were encapsulated in hollow fibers and implanted into animals, thereby producing circulating bovine growth hormone.

3 Claims, No Drawings

ENCAPSULATED MOUSE CELLS TRANSFORMED WITH AVIAN RETROVIRUS-BOVINE GROWTH HORMONE DNA, AND A METHOD OF ADMINISTERING BGH IN VIVO

BACKGROUND OF THE INVENTION

The present invention is directed to the use of novel recombinant DNA molecules in which an avian long terminal repeat (LTR) is ligated to the bovine growth hormone (BGH) gene, and co-transformed into stable mouse fibroblast cell lines containing the recombinant genetic material integrated into the mouse cell genome. These mouse cells can be encapsulated into hollow fibers and implanted into animals (e.g., subcutaneously, intradermally or intraventricularly, etc.), thereby producing circulating bovine growth hormone (BGH).

Copending application Ser. No. 609,923 filed May 14, 1984, filed by the same inventors and assigned to Merck & Co. Inc., discloses and claims the preparation of the plasmids and the mouse cell lines producing BGH.

SUMMARY OF THE INVENTION

Using recombinant DNA techniques, portions of the bovine growth hormone structural gene have been combined with eucaryotic regulatory regions of the Rous Sarcoma Viral genome to produce the materials herein designated as pBGH-3 and pBGH-4; these plasmids have been co-transformed into a mouse cell line; and the mouse cell line encapsulated into hollow fiber units and inserted into animals.

DETAILED DESCRIPTION

Construction of Bovine Growth Hormone-Avian Retroviral DNA hybrids

We have obtained bovine growth hormone genomic DNA in a pBR322 plasmid (pBGH-1). Using recombinant DNA technology, the bovine growth hormone promoter element was removed from the structural gene. This subcloned plasmid lacking a promoter was termed pBGH-2. We have ligated an avian retroviral promoter element, i.e., a viral Long Terminal Repeat (LTR), to the bovine growth hormone structural gene. Ligation was performed at 2 distinct restriction enzyme cleavage sites found within a region of each DNA which encodes 5'-untranslated portions of their m-RNAs. These 5'-untranslated portions of the m-RNAs ("leader" sequences) are nucleotides located between the m-RNA cap site and the translation initiation codon. Bovine growth hormone and avian retroviral 5'-untranslated nucleotide sequences are comprised of 59 base pairs and 379 base pairs, respectively.

These novel plasmid clones have been named pBGH-3 and pBGH-4.

Construction of Recombinant Plasmid, pBGH-3

Plasmid DNAs (bovine growth hormone and Rous Sarcoma Virus) were transfected into $E.$ $coli$ RRl cells. Clones were isolated and the plasmid DNAs amplified. The resulting DNAs were characterized using diagnostic endodeoxyribonuclease recognition sites based on restriction enzyme maps available for the original clones. We have termed these plasmids pBGH-1 (plasmid bovine growth hormone-1) and pL397 (Rous Sarcoma Virus).

pBGH-1 (10 μg) was digested to completion with Bam HI and SalI. Two linear DNA fragments of μ5.0 kb and μ3.0 kb resulted. The fragements were separated by agarose gel electrophoresis (1% Seaplaque agarose). The larger fragment containing the bovine growth hormone gene was eluted from the gel. To insure purity, this DNA again was subjected to agarose gel electrophoresis (1% Seaplaque) and elution. Approximately 500 ng was recovered.

Rous Sarcoma virus clone pL397 was enzymatically cleaved with BamHI and the five resulting linear DNA fragments separated by agarose gel electrophoresis (1% Seaplaque). A linear fragment of μ6.0 kb was eluted from the gel, enzymatically digested with SalI, and subjected to a similar agarose gel electrophoresis procedure. Approximately 2.0 kb linear DNA fragment encoding the avian retroviral LTR (promoter) was purified. Approximately, 500 ng of DNA was recovered.

Ligation of the viral DNA sequences to the bovine growth hormone gene occurred at a BamHI site. Viral sequences include the 3' portion of the 'env' gene, the viral LTR, approximately 530 nucleotides of the viral leader sequence and 5' portion of the viral 'gag' gene. Included in the bovine growth hormone segment of the recombinant plasmid are the 5 bovine growth hormone exons (shown in boxes) as well as μ500 base pairs found at the 3' terminus of the gene.

100 ng of DNA containing equimolar quantities of the above isolated DNA fragments were ligated for 1 hour at 22° C. Following transfection into $E.$ $coli$ RRl cells, 100 colonies were isolated. Non-ligated control DNA preparations resulted in zero colonies.

Restriction enzymatic digestion analysis of this cloned DNA confirmed that the two segments of the above mentioned DNAs were joined, thus creating a new biological molecule. This molecule has been termed pBGH-3.

Construction of Recombinant Plasmid, pBGH-4

In order to alter pBGH-3 such that non-essential regions of the Rous Sarcoma derived DNA were removed, the following procedure was followed.

A large 7.0 kb linear DNA fragment derived from pBGH-3 by BSTEII and BamHI cleavage was purified by agarose gel electrophoresis. Following excision from the gel, the DNA was treated with $E.$ $coli$ DNA polymerase (Klenow large fragment) which resulted in the generation of molecules possessing flush termini. Blunt end ligation of these molecules and transfection into $E.$ $coli$ RRl cells resulted in bacterial clones containing plasmid DNA similar to that of pBGH-3. However approximately 430 base pairs between the viral BSTEII and BamHI sites have been deleted. Restriction enzymatic digestion analysis of this cloned DNA confirmed that this non-essential region of the pBGH-3 had been removed. This plasmid has been designate pBGH-4.

Sequencing of pBGH-4

The DNA nucleotide sequencing of pBGH-4 was done in the following manner: pBGH-4- DNA (20 ng) was cleaved with EcoRI resulting in 3 linear DNA fragments of 4.3 kb, 2.15 kb, and 1.5 kb. The 2.15 kb DNA molecule was isolated by agarose gel electrophoresis (1% Seaplaque agarose). Following elution of the DNA from the agarose gel, the 5' protruding termini were labeled by addition of α-5' ($^{32}$P) dATP using $E.$ $coli$ DNA polymerase I (Klenow fragment). The $^{32}$P labeled DNA molecule was cleaved subsequently with SmaI yielding 2 DNA molecules of 2.0 kb and 0.5 kb in size. The DNA molecule containing 2.0 kb was purified by agarose gel electrophoresis (1% Seaplaque agarose) and sequenced according to the procedure of Maxam and Gilbert, *Proc. Natl. Acad. Sci.* U.S.A., 74: 560–564 (1977). The junction between the RSV-LTR and the bovine growth hormone gene was confirmed to be the predicted sequence:

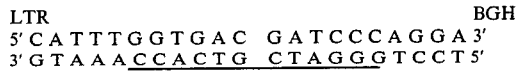

```
LTR                              BGH
5' C A T T T G G T G A C   G A T C C C A G G A 3'
3' G T A A A C C A C T G   C T A G G G T C C T 5'
```

Transient Assay for Screening Plasmid Constructs

We have also developed a rapid and sensitive transient assay system for the detection of bovine growth hormone by cultured rat GH3 cells transfected with plasmid DNA encoding bovine growth hormone, to quickly screen a variety of plasmid constructs for their ability to direct the synthesis of BGH. We have shown and confirmed that pBGH-4 directs the synthesis and secretion of bovine growth hormone by these cells.

The optimum conditions for the transient expression of bovine growth hormone by rat GH3 cells have been determined.

It has been reported in the literature that DNA transfection of cultured cells mediated by DEAE-Dextran is influenced by at least two parameters. They are (1) the concentration of DNA used in the experiment and (2) the length of time cells are exposed to the DEAE-Dextran-DNA complex. We have optimized our transient assay system in rat GH3 relative to these two parameters.

Briefly about $5.0 \times 10^5$ rat GH3 cells were plated onto 35 mm tissue culture plates. Following overnight incubation, cells were rinsed with 2.0 ml culture fluid minus serum. 1.0 Ml of culture fluid minus serum containing a variety of concentrations of pBGH-4 DNA along with DEAE-Dextran (200 µg/ml) was added to the cells. Following incubation at 37° C. for a variety of time intervals, the DEAE-Dextran-DNA solution was removed and the cells rinsed two times with complete medium. Cells were incubated for 5 days with changes in cultured fluid at daily intervals. Bovine growth hormone was assayed in the culture fluid using a sensitive radioimmunoassay.

Using this assay, pBGH-4 directed detectable levels of bovine growth hormone, detectable at 48 hours and 72 hours post transfection. Increasing amount of DNA in the DEAE-DNA complex used per transfection resulted in a respective elevation in BGH secretion. At 72 hours, cells exposed to 500 ng of DNA produced approximately 10 fold more (283.8 ng/ml) BGH relative to these exposed to 250 ng DNA, (30 ng/ml).

In a similar manner the amount of time to which the cells were exposed to the DEAE-Dextran-DNA mixture was altered. In this experiment, 250 ng of DNA was used in each transfection. Bovine growth hormone expression varied inversely with the duration of transfection time.

From these and other related experiments, and although results do vary from one set of experiments to another, it is concluded that pBGH-4 DNA directs the synthesis of detectable levels of bovine growth hormone by cultured rat GH3 cells following DEAE-Dextran mediated transfection.

The optimum amount of DNA used in these transfection experiments ranged from 250 ng to 500 ng per $5 \times 10^5$ cells.

Time intervals of DEAE-Dextran-DNA exposure to GH3 cells between 30 minutes and 45 minutes are optimal for subsequent expression of bovine growth hormone.

Production of Mouse Cell Lines Secreting Bovine Growth Hormone

In order to produce a large amount of purified BGH protein, we generated cultured mouse fibroblasts secreting the BGH. This was performed by co-transforming mouse TK(−) L cells with Herpes Viral TK DNA and plasmid vectors capable of directing BGH expression as determined by our transient assay. After selecting for a TK(+) phenotype, plasmids encoding BGH will be present and active in directing the expression of Bovine Growth Hormone.

To $5 \times 10^5$ mouse L cells (LTK−, APRT−) was added a complex of calcium phosphate precipitated DNA. Included in the complex was 10 µg of L cell (LTK−, APRT−) DNA, 10 µg of pBGH-4 DNA, and 100 ng of pTK5 DNA. Ten TK positive colonies were selected and subcultured. The amount of bovine growth hormone secreted into the culture fluid was determined. Culture L-BGH-4-3 is secreting about 3.0 µg BGH per $5 \times 10^6$ cells, per 24 hours.

In order to generate a mouse cell line which secrete a larger quantity of BGH, an alternative approach was performed. The protocol involves cotransformation of mouse-L-cells (TK−, APRT−) by a plasmid DNA which encodes the APRT gene and a truncated TK gene, PdλAT-3, (Robert & Axel, 1982) along with plasmid pBGH-4 DNA. Results from these types of cotransformation experiments have revealed that plasmid DNA involved in the cotransformation are amplified within the mouse cell following transfection. Amplification of the plasmid DNA results in a corresponding amplification of gene product.

Briefly, $5 \times 10^5$ cells are cotransformed, using the CaPO$_4$ method above, with PdλAT3 (20 ng) and BGH-4 (2 µg) DNA. The cells are first selected in DME plus 10% CS plus 4 µg/ml azaserine, plus 15 µg/ml adenine for selection of the APRT+phenotype. These APRT+cells are then selected in DME plus 10% CS plus 15 µg/ml hypoxanthine plus 1 µg/ml aminopterin plus 5.15 µg/ml thymidine for selection of the TK+phenotype. The APRT+, TK+ cells are subsequently screened for their ability to secrete BGH. Twenty stable positive colonies were generated and subcultured. The amount of BGH secreted into the culture fluid was determined. Culture L-BGH-4-13 is secreting 75 g BGH per $5 \times 10^6$ cells per 24 hours.

BGH produced by these cells can be purified as known in the art and used as designed, e.g., as a growth stimulant in animals, see EPO No. 0085036, Monsanto, and EPO No. 0068646, Upjohn.

Two mouse L-cell lines stably tranformed with pBGH-4 DNA and expressing large amounts of BGH as well as plasmids pBGH-3 and pBGH-4 have been deposited at the ATCC, and are available to be public upon the grant of a patent to the assignee, Merck & Co. Inc., disclosing these. These deposits are also available as required by Foreign Patent laws in countries wherein counterpart applications are filed. The deposit numbers are ATCC CRL 8536 and ATCC CRL-8537, for the mouse cell cultures BGH-4-13 and BGH-4-3, respectively, deposited Apr. 6, 1984; and ATCC 39674 and ATCC 39675, for pBGH-3 and pBGH-4, respectively.

The highly important use of the mouse cell lines L-BGH-4-3 and L-BGH-4-13 secreting bovine growth hormone is in a hollow fiber delivery system, which can be implanted into many commercially important animal species, such as chickens, turkeys, cattle, swine, and sheep.

In vitro Expression of Bovine Growth Hormone by Mouse Cells Encapsulated in a Hollow Fiber Unit The mouse cell line L-BGH-4-3 described above was loaded into a hollow fiber (polyvinylchloride-acrylic copolymer, XM-50 manufactured and sold by Amicon). This fiber has a 1100 $\mu$m internal diameter and is approximately 10 mm long. The Scanning Electron Micrograph (SEM) of the fiber, see Hymer et al., Neuroendocrinology, 32: 339-349 (1981), "Pituitary Hollow Fiber Units in vivo and in vitro," shows the spongy layer of polymer with increasing openings to one fiber periphery. Each fiber unit was loaded with 7-8 $\mu$l of a mouse cell suspension (L-pBGH-4-3) containing about 250,000 cells/$\mu$l. Following encapsulation, the ends of the hollow fiber were sealed and incubated in 35 mm culture dishes with DMED medium. Media were collected at various time intervals and analyzed for BGH by a BGH RIA. BGH was detected in the culture fluid 48 hours after the capsules were plated in culture dishes. The cells within the fiber were secreting BGH 75 days post encapsulation. The amounts of BGH measured by RIA are in direct correlation with the number of capsules incubated.

This is a novel in vitro system in which eucaryotic cells producing BGH can be analyzed by using these hollow fibers.

The fiber-mouse cell line L-BGH-4-3 system could be used to produce and purify BGH simply by allowing the cells to secrete GH through the fiber filter unit into an appropriate medium. The hollow fiber unit containing a recombinant mouse cell suspension is capable of producing bovine growth hormone in an amount sufficient to stimulate animal growth or milk production when implanted in an animal. The cell suspension which has been previously transfected with biologically active DNA thus is capable of producing the protein that the cells have been selected to produce and secrete in a biologically active amount when implanted in an animal.

The fibers could also usefully be implanted into animals. BGH has been shown to stimulate milk production in dairy cattle, see Machlin, *J. Dairy Sci.*, Vol 56, No. 5, p. 575; C. J. Peel, et al., J. Nutr. (1981), 111 (9) 1662-1671; see also EPO application No. 85036, published Aug. 3, 1983.

When these fibers are implanted into poultry such as chickens, and small mammals, such as rats, BGH is detected in the circulatory system.

The fibers can also be implanted, either subcutaneously, intradermally or intraventricularly, etc., into large animals, especially those valuable as milk producers, such as dairy cows. An effective amount of BGH to stimulate milk production is 0.005 to 200,000 $\mu$g per animal per day, and this amount can be produced by selected fiber units containing the BGH-producing mouse cell line. See also EPO 0085036, herein incorporated by reference, for amounts and regimine of administration.

In addition to the specific example in this application, using one encapsulated mouse cell line cotransformed with bovine growth hormone gene, to produce BGH when implanted, it will be apparent to those skilled in the art that any eucaryotic cells transfected with biologically active DNA and secreting corresponding proteins can be put into the polyvinylchloride-acrylic copolymer fibers described. Specifically, any of the BGH expression systems claimed in GB No. 2073245 (Yeda), EPO No. 0085 036 (Monsanto), EPO No. 0067 026 (Michigan State), or EPO No. 0068 646 (Upjohn) can be inserted into the mouse cell line herein described, or any other suitable cell line, encapsulated in the fiber; and implanted in any animal.

Also, other cell lines producing other hormones or proteins can be encapsulated in these fibers and used as herein described. Even more generally, any eucaryotic cell can be transfected with biologically active DNA, the particular cell selected and cloned for production, expression and secretion of the corresponding protein product; and these cells encapsulated as herein described. Examples of other proteins expressed by cell lines to which the methodology of this invention is applicable include human serum albumin, human interferons, human antibodies, human insulin, blood clotting factors, human growth factors, brain peptides, enzymes, hormones, prolactin, viral antigens and plant proteins.

What is claimed is:

1. The method for increasing animal growth by implantation in vivo in cows an effective amount of the encapsulated cell line L-BGH-4-3, ATCC CRL 8537 or L-BGH-4-13, ATCC CRL-8536.

2. The method of claim 1 in which the encapsulated cell line is implanted subcutaneously.

3. A hollow fiber, about 10 mm long polyvinyl chloride-acrylic copolymer, having about a 1100 $\mu$m internal diameter, containing a recombinant mouse cell suspension capable of producing bovine growth hormone in an amount sufficient to stimulate animal growth or milk production when implanted in an animal.

* * * * *